United States Patent [19]

Chan et al.

[11] Patent Number: 4,521,335

[45] Date of Patent: Jun. 4, 1985

[54] AGLYCONE AND PSEUDO-AGLYCONES OF THE AAD 216 ANTIBIOTICS

[75] Inventors: George W. Chan, Bala Cynwyd; Robert D. Sitrin, Plymouth Meeting, both of Pa.

[73] Assignee: SmithKline Beckman Corporation, Philadelphia, Pa.

[21] Appl. No.: 611,070

[22] Filed: May 17, 1984

Related U.S. Application Data

[63] Continuation-in-part of Ser. No. 513,514, Jul. 13, 1983.

[51] Int. Cl.$^3$ ............................................. C07C 103/52
[52] U.S. Cl. ............................................. 260/112.5 R
[58] Field of Search ................................. '260/112.5 R

[56] References Cited

U.S. PATENT DOCUMENTS 4,322,343  3/1982  Debono ..................... 260/112.5 R

OTHER PUBLICATIONS

Williams et al., "Topics in Antibiotic Chemistry", vol. 5, pp. 119–158.

Primary Examiner—Delbert R. Phillips
Attorney, Agent, or Firm—Edward T. Lentz; Janice E. Williams; Alan D. Lourie

[57] ABSTRACT

Novel aglycone and pseudo-aglycones of the AAD 216 antibiotics are prepared by partial acid hydrolysis of the AAD 216 antibiotic complex or its individual factor antibiotics. AAD 216 aglycone, AAD 216 pseudo-aglycone and AAD 216A pseudo-aglycone, AAD 216B pseudo-aglycone and AAD 216C pseudo-aglycone exhibit antibacterial activity and are useful in animal health applications.

6 Claims, No Drawings

AGLYCONE AND PSEUDO-AGLYCONES OF THE AAD 216 ANTIBIOTICS

This is a continuation-in-part of application Ser. No. 513,514 filed on July 13, 1983.

BACKGROUND OF THE INVENTION

Novel AAD 216 antibiotics of the vancomycin-class are produced by cultivating the new microorganism, *Kibdelosporangium aridium* Shearer, gen. nov., sp. nov. SK&F AAD 216 (ATCC 39323) in aqueous nutrient medium, containing assimilable sources of carbon and nitrogen, under submerged aerobic conditions until a substantial amount of the AAD 216 antibiotic complex is produced and optionally recovering the AAD 216 complex from the culture medium and isolating the individual major antibiotic factors, AAD 216A, AAD 216B, and AAD 216C. The AAD 216 antibiotics and the microorganism, *K. aridium*, are disclosed and claimed in co-pending U.S. patent application Ser. No. 513,513 filed on July 13, 1983.

SUMMARY OF THE INVENTION

This invention relates to the novel aglycone and pseudo-aglycones of the AAD 216 antibiotics which are prepared by the partial acid hydrolysis of the AAD 216 antibiotic complex or the individual antibiotic factors which comprise the AAD 216 complex followed by chromatographic isolation. The compounds of this invention exhibit antibacterial activity and are useful in animal health applications such as growth promotants and the treatment of bovine mastitis.

DETAILED DESCRIPTION OF THE INVENTION

The aglycone and pseudo-aglycones of the instant invention are prepared by the partial acidic hydrolysis of the AAD 216 antibiotics, which for the purpose of the present application is defined as the AAD 216 antibiotic complex and its major individual antibiotic factors, AAD 216A, AAD 216B and AAD 216C. The aglycone and the pseudo-aglycones of the AAD 216 antibiotics are represented by the following general structural formula (I):

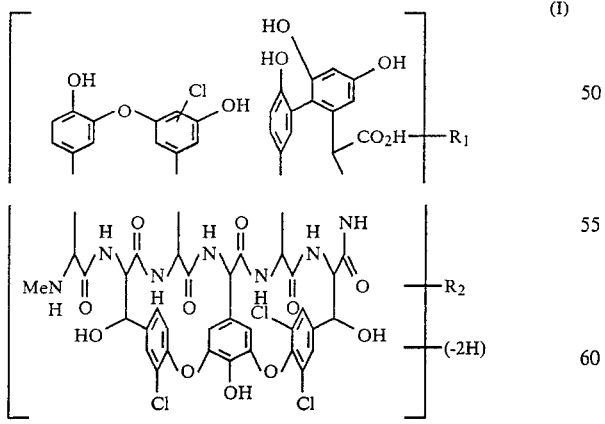

wherein $R_1$ is hydrogen or a mannosyl radical and $R_2$ is hydrogen or a glycolipid radical of unknown structure derived from the hydrolyzed AAD 216 antibiotic with the proviso that at least one of $R_1$ and $R_2$ is hydrogen. The AAD 216 antibiotic complex is the compound of formula (I) wherein $R_1$ is mannosyl and $R_2$ is a glycolipid radical.

The hydrolysis of the AAD 216 antibiotics proceeds along two pathways to afford the AAD 216 aglycone of the formula (I) wherein $R_1$ and $R_2$ are hydrogen as follows:

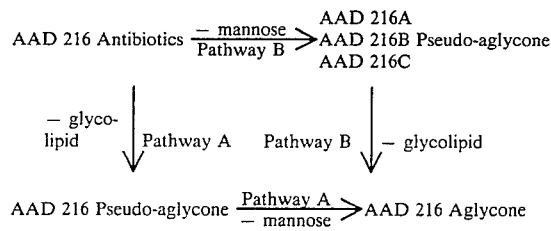

The initial step of the hydrolysis pathway A involves the loss of the glycolipid radicals from the AAD 216 antibiotics to yield the pseudo-aglycone of formula (I) wherein $R_1$ is mannosyl and $R_2$ is hydrogen. This pseudo-aglycone is denominated AAD 216 pseudo-aglycone since it is independent of which AAD 216 antibiotic is hydrolyzed. Subsequent hydrolysis of the AAD 216 pseudo-agylcone yields the AAD 216 aglycone upon the loss of the mannosyl radical.

The initial step of the hydrolysis pathway B involves the loss of the mannosyl radical from the AAD 216 antibiotics to give pseudo-aglycones of the formula (I) wherein $R_1$ is hydrogen and $R_2$ is a glycolipid radical of unknown structure which is derived from the AAD 216 antibiotic factor hydrolyzed. Accordingly, these pseudo-aglycones are denominated AAD 216A pseudo-aglycone, AAD 216B pseudo-aglycone or AAD 216C pseudo-aglycone depending on the AAD 216 antibiotic factor hydrolyzed. Where the AAD 216 complex is hydrolyzed, a mixture of these pseudo-aglycones will result.

The AAD 216A pseudo-aglycone contains a glycolipid radical of unknown structure with a molecular weight of 330 amu and an empirical formula of $C_{16}H_{28}NO_6$. The methanolysis of AAD 216A pseudo-aglycone produced two major products which were identified as the methylglycosidemethyl ester of an n-decanoyldeoxyaminoglycuronic acid and the methylglycoside of either n-decanoyldeoxyaminoglycofurano-3,6-lactone or n-decanoyldeoxyaminoglycopyrano-3,6-lactone. The diacetate derivative of first major methanolysis product of AAD 216A pseudo-aglycone was compared with and found to be identical to the diacetate derivative of methyl-2-deoxy-2[(1-oxodecyl)amino]-α-D-glycopyranosiduronic acid methyl ester, which was prepared in a simple two-step process from D-glucosamine. From the above evidence, the structure of the glycolipid radical of AAD 216A pseudo-aglycone is most probably as follows:

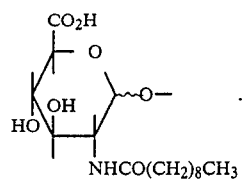

Since AAD 216A, AAD 216B and AAD 216C are homologs, the glycolipid radicals of AAD 216B pseudo-aglycone and AAD 216C pseudo-aglycone have molecular weights of 344 and 358, respectively, and empirical formulae of $C_{17}H_{30}NO_6$ and $C_{18}H_{32}NO_6$, respectively. Utilizing comparative studies of the $^{13}C$ nuclear magnetic resonance spectra of AAD 216A, AAD 216B and AAD 216C as well as a comparative studies of the fatty acid hydrolysis products of the parent antibiotic factors, the glycolipid radicals of AAD 216B pseudo-aglycone and AAD 216C pseudo-aglycone are tentatively assigned the following respective structures:

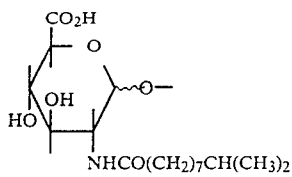

and

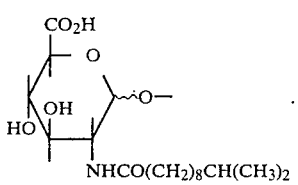

The AAD 216 pseudo-aglycone of the formula (I) wherein $R_1$ is mannosyl and $R_2$ is hydrogen has the following characteristics:

(a) pale white-yellow solid which decomposes at 300°–350° C.;

(b) an empirical formula $C_{65}H_{55}N_7O_{24}Cl_4$;

(c) an approximate elemental composition of 47.54 percent carbon, 4.00 percent hydrogen, 5.89 percent nitrogen and 8.63 percent chlorine when the water content was 12 percent;

(d) an infrared absorption spectrum in potassium bromide which exhibits peaks at the following wave numbers in $cm^{-1}$: 3400, 1660, 1610, 1590, 1510, 1460, 1430, 1390, 1300, 1230, 1180, 1150, 1120, 1060, 1010, 970 and 810;

(e) a fast atom bombardment (FAB) mass spectrum with M+H at 1458 (major cluster);

(f) an ultraviolet spectrum in acetonitrile:water (1:1) which exhibits an absorption maximum at 281 nm under acid conditions with an $E_{1\%}=79.7$ and at 300 nm under basic conditions with an $E_{1\%}=136$;

(g) a carbon magnetic resonance spectrum at 90.56 MHz in $CD_3OD:D_2O$ (1:9) at a pH of 8.7 which exhibits the following chemical shifts in parts per million (ppm) relative to TMS as standard: 177.9, 174.6, 171.7, 170.9, 170.0, 169.2, 162.3, 158.8, 157.9, 155.2, 155.1, 153.9, 151.9, 149.7, 147.6, 147.2, 144.4, 141.0, 139.0, 138.8, 137.5, 136.1, 134.6, 130.7, 130.0, 129.8, 129.2, 128.9, 128.7, 127.5, 127.3, 126.9, 126.4, 126.0, 125.2, 122.7, 122.2, 121.1, 119.9, 119.7, 118.4, 116.6, 110.7, 110.4, 108.5, 104.4, 103.3, 100.5, 98.1, 74.0, 72.1, 71.6, 71.4, 70.8, 67.4, 65.8, 63.7, 62.2, 61.6, 60.2, 56.0, 55.9, 55.0 and 32.9; and (h) $pK_a$ values in acetonitrile:water (3:7) as follows: 3.3, 7.1, 8.3, 9.1, 10.0 and 11.2 $pK_a$ values above 11.2 not determined.

The AAD 216A pseudo-aglycone of the formula (I) wherein $R_1$ is hydrogen and $R_2$ is a glycolipid of unknown structure having an empirical formula $C_{16}H_{28}NO_6$ has the following characteristics:

(a) pale white-yellow solid which decomposes at 300°–350° C.;

(b) an empirical formula $C_{75}H_{72}N_8O_{25}Cl_4$;

(c) an approximate elemental composition of 49.76 percent carbon, 4.51 percent hydrogen, 5.99 percent nitrogen and 8.19 percent chlorine when the water content was 9.4 percent;

(d) an infrared absorption spectrum in potassium bromide which exhibits peaks at the following wave numbers in $cm^{-1}$: 3400, 2920, 1660, 1590, 1500, 1460, 1430, 1300, 1240, 1140, 1080, 1060 and 1010;

(e) a fast atom bombardment (FAB) mass spectrum with M+H at 1625 (major cluster);

(f) an ultraviolet spectrum in acetonitrile:water (1:1) which exhibits an absorption maximum at 281 nm under acidic conditions with an $E_{1\%}=63.2$ and at 302 nm under basic conditions with an $E_{1\%}=94$;

(g) a carbon magnetic resonance spectrum at 90.56 MHz in $CD_3OD:D_2O$ (1:9) at a pH of 9.4 which exhibits the following chemical shifts in parts per million (ppm) relative to TMS as standard: 178.2, 178.0, 176.0, 175.6, 171.6, 170.9, 170.6, 170.5, 169.3, 164.6, 161.4, 159.3, 157.1, 156.5, 153.5, 152.5, 151.8, 151.1, 146.4, 144.9, 141.7, 138.6, 138.4, 136.9, 134.5, 134.4, 133.9, 130.8, 129.8, 129.7, 129.4, 128.6, 128.5, 128.3, 127.7, 127.3, 125.9, 125.7, 125.5, 122.5, 122.1, 120.1, 119.4, 118.0, 116.9, 109.6, 109.0, 108.7, 104.5, 104.4, 103.2, 98.9, 78.4, 74.3, 73.3, 72.1, 71.5, 66.2, 63.7, 61.9, 60.6, 56.9, 56.1, 55.8, 55.4, 37.2, 33.3, 32.0, 29.6, 29.4, 26.1, 22.9 and 14.4; and (h) $pK_a$ values in acetonitrile:water (3:7) as follows: 3.0, 4.3, 7.4, 8.5, 9.9 and 10.9 $pK_a$ values above 10.9 not determined.

The AAD 216B pseudo-aglycone of the formula (I) wherein $R_1$ is hydrogen and $R_2$ is a glycolipid radical of unknown structure having an empirical formula $C_{17}H_{30}NO_6$ has the following characteristics:

(a) white solid which decomposes at 250°–300° C.;

(b) an empirical formula $C_{76}H_{74}N_8O_{25}Cl_4$;

(c) an approximate elemental composition of 48.98 percent carbon, 4.56 percent hydrogen, 5.64 percent nitrogen and 8.29 percent chlorine when the water content was 6.9 percent;

(d) an infrared absorption spectrum in potassium bromide which exhibits peaks at the following wave numbers in $cm^{-1}$: 3400, 2920, 1660, 1590, 1500, 1480, 1430, 1300, 1240, 1150, 1080, 1060 and 1010;

(e) a fast atom bombardment (FAB) mass spectrum with M+H at 1639 (major cluster);

(f) an ultraviolet spectrum in acetonitrile:water (1:1) which exhibits an absorption maximum at 281 nm under acidic conditions with an $E_{1\%}=61.8$ and at 303 nm under basic conditions with an $E_{1\%}=88$;

(g) a carbon magnetic resonance spectrum at 90.56 MHz in $CD_3OD:D_2O$ (1:9) at a pH of 9.4 which exhibits the following chemical shifts in parts per million (ppm) relative to TMS as standard: 178.3, 177.6, 175.9, 175.6, 171.5, 171.0, 170.7, 170.3, 169.4, 164.0, 159.3, 158.9, 156.4, 152.5, 151.7, 151.1, 146.2, 144.7, 141.8, 138.7, 138.6, 136.8, 134.4, 133.8, 130.9, 129.8, 129.5, 128.6, 128.4, 127.9, 127.3, 126.0, 125.8, 122.5, 119.9, 119.3, 118.2, 116.9, 109.3, 108.8, 104.3, 104.2, 103.0, 99.4, 78.7, 74.4, 73.5, 72.1, 71.6, 65.8, 63.8, 62.5, 60.6, 57.1, 56.1, 55.9, 55.4, 39.7, 37.3, 33.1, 30.3, 29.9, 29.7, 28.5, 28.0, 26.3 and 23.4.

The AAD 216C pseudo-aglycone of the formula (I) wherein $R_1$ is hydrogen and $R_2$ is a glycolipid radical of unknown structure having an empirical formula $C_{18}H_{32}NO_6$ has the following characteristics:

(a) white solid which decomposes at 250°–300° C.;

(b) an empirical formula $C_{77}H_{76}N_8O_{25}Cl_4$;

(c) an approximate elemental composition of 47.58 percent carbon, 4.51 percent hydrogen, 5.33 percent nitrogen and 8.08 percent chlorine when the water content was 7.8 percent;

(d) an infrared absorption spectrum in potassium bromide which exhibits peaks at the following wave numbers in $cm^{-1}$: 3400, 2920, 1660, 1590, 1500, 1430, 1300, 1240, 1140, 1080, 1060 and 1010;

(e) a fast atom bombardment (FAB) mass spectrum with M+H at 1653 (major cluster);

(f) an ultraviolet spectrum in acetonitrile:water (1:1) which exhibits an absorption maximum at 281 nm under acidic conditions with an $E_{1\%}=60.0$ and at 303 nm under basic conditions with an $E_{1\%}=83$;

(g) a carbon magnetic resonance spectrum at 90.56 MHz in $CD_3OD:D_2O$ (1:9) at a pH of 9.4 which exhibits the following chemical shifts in parts per million (ppm) relative to TMS as standard: 178.1, 177.4, 175.5, 175.4, 171.4, 171.0, 170.7, 170.3, 169.3, 163.6, 159.1, 158.6, 156.5, 156.2, 152.7, 151.9, 151.8, 151.0, 146.2, 144.6, 142.0, 138.8, 138.6, 136.9, 134.8, 134.7, 134.0, 130.6, 129.9, 129.8, 129.4, 128.8, 128.3, 127.8, 127.5, 127.2, 126.4, 126.2, 125.8, 122.5, 122.0, 119.6, 119.1, 118.4, 116.9, 109.5, 109.2, 108.7, 104.2, 103.6, 99.8, 78.6, 74.6, 73.5, 72.1, 71.7, 66.0, 63.7, 62.1, 60.6, 56.9, 56.1, 55.9, 55.4, 39.6, 37.3, 33.2, 30.4, 30.0, 29.8, 28.5, 27.9, 26.3 and 23.1.

The AAD 216 aglycone, represented by the structural formula (II)

acidic conditions with an $E_{1\%}=83$ and at 300 nm under basic conditions with an $E_{1\%}=140$;

(g) a carbon magnetic resonance spectrum at 90.56 MHz in $(CD_3)_2SO$ at a pH of 3.3 which exhibits the following chemical shifts in parts per million (ppm) using TMS as the internal standard: 172.6, 172.1, 170.0, 169.2, 168.4, 167.2, 167.0, 157.2, 156.4, 155.5, 155.0, 154.6, 151.4, 147.5, 145.8, 144.7, 142.8, 141.7, 139.0, 138.7, 136.2, 135.6, 134.5, 128.5, 128.2, 128.0, 127.9, 127.8, 127.4, 127.3, 126.3, 126.0, 125.3, 125.0, 121.1, 118.1, 117.7, 117.5, 116.6, 113.7, 108.7, 106.3, 105.9, 105.4, 103.7, 102.5, 71.3, 70.1, 65.3, 61.4, 60.1, 56.8, 54.8, 53.9, 53.6 and 33.4; and (h) $pK_a$ values in acetonitrile:water (3:7) as follows: 3.3, 7.1, 8.4, 9.2, 10.1 and 11.4 $pK_a$ values above 11.4 not determined.

The compounds of the instant invention are conveniently prepared from the AAD 216 antibiotics along the following lines:

The AAD 216 pseudo-aglycone is prepared by hydrolyzing the AAD 216 antibiotics, exemplified by AAD 216A, in aqueous organic solvent and very dilute mineral acid at reflux until a substantial amount of the AAD 216 pseudo-aglycone is formed and subsequently isolating it from the reaction mixture. Illustrative of this hydrolysis process is the treatment of AAD 216A in 10 percent aqueous acetonitrile with 0.001N hydrochloric at reflux for 48 hours and the isolation of the AAD 216 pseudo-aglycone by chromatographic means.

The AAD 216 aglycone, the AAD 216A pseudo-aglycone, AAD 216B pseudo-aglycone and AAD 216C pseudo-aglycone are prepared by the hydrolysis of the appropriate AAD 216A, AAD 216B and AAD 216C in

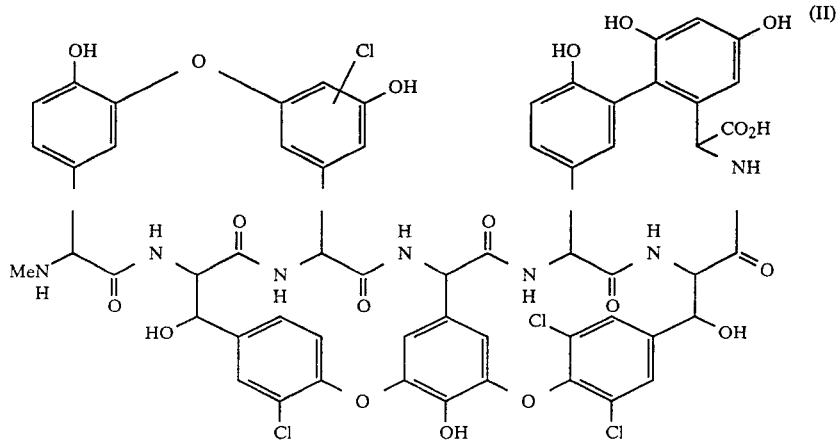

has the following characteristics:

(a) pale white-yellow solid which decomposes at 300° to 350° C.;

(b) an empirical formula $C_{59}H_{45}N_7O_{19}Cl_4$;

(c) an approximate elemental composition of 47.92 percent carbon, 3.78 percent hydrogen, 6.58 percent nitrogen and 9.50 percent chlorine when the water content is 10.70 percent;

(d) an infrared absorption spectrum in potassium bromide which exhibits peaks at the following wave numbers in $cm^{-1}$: 3400, 1660, 1610, 1590, 1510, 1460, 1430, 1390, 1300, 1240, 1150, 1080, 1060 and 1010;

(e) a fast atom bombardment (FAB) mass spectrum with M+H at 1296 (major cluster);

(f) an ultraviolet spectrum in acetonitrile:water (1:1) which exhibits an absorption maximum at 281 nm under a polar organic solvent and dilute mineral acid at elevated temperature until a substantial amount of the hydrolysis products are formed and subsequently isolating the individual desired products. Illustrative of this hydrolysis process is the treatment of AAD 216A in dimethylsulfoxide with 5 percent hydrochloric acid at 100° C. for 15 minutes. The isolation of the individual AAD 216 aglycone and the AAD 216A pseudo-aglycone may be accomplished by chromatographic means.

Alternatively, the AAD 216 aglycone and the pseudo-aglycones may be prepared by the mild acid hydrolysis of the AAD 216 complex or the individual factors followed by a chromatographic isolation of the desired compounds.

BIOLOGICAL ACTIVITY DATA

The in vitro minimum inhibitory concentrations (MIC) of the AAD 216 aglycone, AAD 216 pseudo-aglycone, AAD 216A pseudo-aglycone, AAD 216B pseudo-aglycone, AAD 216C pseudo-aglycone and vancomycin were determined for a number of microorganisms using the standard microtiter assay procedures. The AAD 216 aglycone, the AAD 216 pseudo-aglycone, the AAD 216A pseudo-aglycone, the AAD 216B pseudo-aglycone and the AAD 216C pseudo-aglycone were neutralized with sodium bicarbonate prior to testing. The results are shown in the following Tables A-F.

TABLE A

Antimicrobial Spectrum

MIC in μg/ml

| Test Organism | AAD 216 Aglycone | AAD 216 Pseudo-Aglycone | AAD 216A Pseudo-Aglycone | Vancomycin |
|---|---|---|---|---|
| Staph. aureus HH127 | 0.4 | 1.6 | 0.8 | 1.6 |
| Staph. aureus SK & F 910 | 0.4 | 1.6 | 0.4 | 1.6 |
| Strep. faecilis HH34358 | 0.8 | 1.6 | 0.4 | 3.1 |
| Proteus mirabilis SK & F 444 | 25 | 100 | 100 | 100 |
| E. coli 12140 (SK & F 809) | 100 | >100 | >100 | 100 |
| k. pneumoniae 4200 (SK & F 798) | >100 | >100 | >100 | >100 |
| Pseudomonas aeruginosa HH63 | >100 | >100 | >100 | >100 |
| Serratia marcesens ATCC 13880 | >100 | >100 | >100 | >100 |
| Proteus morgani SK & F 179 | >100 | >100 | >100 | >100 |
| Providencia SK & F 276 | >100 | >100 | >100 | >100 |
| Enterobacter cloacae HH31254 | >100 | >100 | >100 | >100 |
| Salmonella gallinarum SK & F BC595 | 25 | 25 | ~100 | 25 |
| Staph. epidermidis SK & F 2479 | 0.8 | ~3.1 | 0.8 | 1.6 |
| Listeria monocytogenes SK & F 2255 | 0.8 | 1.6 | 0.4 | 1.6 |
| Staph. epidermidis SK & F 651 | 3.1 | 12.5 | 3.1 | 1.6 |

TABLE B (Methicillin Sensitive)

MIC in μg/ml

| Test Organism | AAD 216 Aglycone | AAD 216 Pseudo-Aglycone | AAD 216A Pseudo-Aglycone | Vancomycin |
|---|---|---|---|---|
| Staph. aureus HH127 | 0.4 | 1.6 | 0.4 | 1.6 |
| Staph. aureus SK & F 674 | 0.8 | 3.1 | 0.8 | 1.6 |
| Staph. aureus SK & F 910 | 0.8 | 3.1 | 0.4 | 1.6 |
| Staph. aureus SK & F 1761 | 0.8 | 3.1 | 0.4 | 1.6 |
| Staph. aureus SK & F 2666 | 0.8 | 3.1 | 0.4 | 1.6 |
| Staph. aureus SK & F 2677 | 0.8 | 3.1 | 0.4 | 1.6 |
| Staph. aureus SK & F 2678 | 0.8 | 3.1 | 0.4 | 1.6 |
| Staph. aureus SK & F 2680 | 0.8 | 3.1 | 0.8 | 1.6 |
| Staph. aureus SK & F 2682 | 0.8 | 3.1 | 0.4 | 1.6 |
| Staph. aureus SK & F 2736 | 0.8 | 3.1 | 0.8 | 1.6 |
| Staph. aureus SK & F 2743 | 0.8 | 3.1 | 0.8 | 1.6 |
| Staph. aureus SK & F 2776 | 3.1 | 3.1 | 1.6 | 1.6 |
| Staph. aureus SK & F 2777 | 0.4 | 1.6 | 0.4 | 0.8 |
| Staph. aureus SK & F 2613 | 0.4 | 1.6 | 0.4 | 1.6 |
| Staph. aureus SK & F 2615 | 0.8 | 3.1 | 0.8 | 3.1 |

TABLE C (Methicillin Resistant)

MIC in μg/ml

| Test Organism | AAD 216 Aglycone | AAD 216 Pseudo-Aglycone | AAD 216A Pseudo-Aglycone | Vancomycin |
|---|---|---|---|---|
| Staph. aureus SK & F 675 | 0.8 | 3.1 | 0.8 | 1.6 |
| Staph. aureus SK & F 2612 | 0.8 | 3.1 | ~0.8 | 1.6 |
| Staph. aureus SK & F 2614 | 0.4 | 0.8 | 0.2 | 1.6 |
| Staph. aureus SK & F 2616 | 0.4 | 1.6 | 0.2 | 0.8 |
| Staph. aureus SK & F 2620 | 0.8 | 3.1 | 0.8 | 3.1 |
| Staph. aureus SK & F 2621 | 0.4 | 1.6 | 0.4 | 1.6 |
| Staph. aureus SK & F 2594 | 0.4 | 3.1 | 0.4 | 1.6 |
| Staph. aureus SK & F 2589 | 0.4 | 3.1 | 0.4 | 1.6 |
| Staph. aureus SK & F 2590 | 0.4 | 3.1 | 0.4 | 1.6 |
| Staph. aureus SK & F 2593 | 0.8 | 3.1 | 0.8 | 1.6 |
| Staph. aureus SK & F 2591 | 0.8 | 3.1 | 0.8 | 1.6 |
| Staph. aureus SK & F 2592 | 0.8 | 3.1 | 1.6 | 3.1 |
| Staph. aureus SK & F 2595 | 0.8 | 3.1 | 1.6 | 1.6 |
| Staph. aureus SK & F 2596 | 0.4 | 3.1 | 1.6 | 3.1 |
| Staph. aureus SK & F 2597 | 0.8 | 3.1 | 1.6 | 3.1 |

TABLE D (Anaerobes)

MIC in μg/ml

| Test Organism | AAD 216 Aglycone | AAD 216 Pseudo-Aglycone | AAD 216A Pseudo-Aglycone | Vancomycin |
|---|---|---|---|---|
| Bacteroides fragilis ATCC 25285 | 32 | >32 | 16 | 32 |
| B. fragilis H145 | 32 | >32 | 8 | 32 |
| B. fragilis SK & F 3060 | 32 | >32 | 16 | 32 |
| B. loeochis SK & F 3087 | 16 | 32 | 8 | 32 |
| B. thetaiotamicron SK & F 3089 | 32 | >32 | 16 | 32 |
| Fusobacterium nucleatum ATCC 25586 | 32 | >32 | 16 | 32 |
| Clostridium perfringens MCP-1 | ≦0.016 | ≦0.016 | ≦0.016 | 0.5 |
| C. perfringens MCP-2 | <0.016 | 0.031 | <0.016 | 0.5 |
| C. perfringens ATCC 19408 | 0.5 | 0.5 | 0.125 | 1.0 |
| Clostridium difficile SK & F 3062 | 2 | 2 | 0.125 | 2 |

TABLE D-continued (Anaerobes)

| Test Organism | AAD 216 Aglycone | AAD 216 Pseudo-Aglycone | AAD 216A Pseudo-Aglycone | Vancomycin |
|---|---|---|---|---|
| C. difficile SK & F 3065 | 2 | 2 | 0.25 | 4 |
| C. difficile SK & F 3091 | ≦0.016 | ≦0.016 | 0.125 | 2 |
| C. difficile SK & F 3092 | 2 | 2 | 0.125 | 2 |
| C. difficile SK & F 3096 | 1.0 | 2 | 0.25 | 2 |
| C. difficile SK & F 3098 | ≦0.016 | ≦0.016 | ≦0.016 | 2 |

TABLE E

MIC in μg/ml

| Test Organism | AAD 216A Pseudo-Aglycone | AAD 216B Pseudo-Aglycone | AAD 216C Pseudo-Aglycone | Vancomycin |
|---|---|---|---|---|
| Staph. aureus HH127 | 0.4 | 0.4 | 0.2 | 1.6 |
| Staph. aureus SK & F 910 | 0.4 | 0.2 | 0.8 | 1.6 |
| Staph. aureus SK & F 209P | 0.1 | 0.2 | 0.1 | 1.6 |
| Staph. aureus SK & F 209P-mutant | 100 | 50 | 50 | 100 |
| Staph. aureus SK & F 674-P6-mutant | 50 | 50 | 25 | 100 |
| Staph. aureus SK & F 675 | 1.6 | 1.6 | 3.1 | 3.1 |
| Staph. epidermidis SK & F 2479 | 3.1 | 6.3 | 6.3 | 3.1 |
| Staph. epidermidis SK & F 651 | 6.3 | 3.1 | 6.3 | 3.1 |
| Staph. epidermidis SK & F 651 | 12.5 | 12.5 | 12.5 | 3.1 |
| Staph. epidermidis SK & F 2265 | 12.5 | 6.3 | 12.5 | 3.1 |
| Strep. faecalis SK & F 34358 | 0.2 | 0.1 | 0.1 | 3.1 |
| Strep. faecalis SK & F 657 | 0.4 | 0.1 | 0.1 | 3.1 |
| Listeria monocytogenes SK & F 2255 | 0.1 | 0.1 | 0.1 | 0.8 |
| E. coli SK & F 12140 | >100 | >100 | >100 | >100 |
| Salmonella gallinarum BC-595 | >100 | >100 | >100 | >100 |

TABLE F

MIC in μg/ml

| Test Organism | AAD 216A Pseudo-Aglycone | AAD 216B Pseudo-Aglycone | AAD 216C Pseudo-Aglycone | Vancomycin |
|---|---|---|---|---|
| Bacteroides Fragilis ATCC | >32 | >32 | 32 | >32 |
| B. thetaiotomicron H-145 | >32 | >32 | >32 | >32 |
| Fusobacterium nucleatum ATCC 25586 | >32 | 16 | 16 | 32 |
| C. perfringens SK & F 2769 | 0.063 | 0.031 | 0.125 | 0.5 |
| C. perfringens MCP-2 | 0.5 | 0.5 | 0.5 | 2.0 |
| C. difficile SK & F 3062 | 0.125 | 0.125 | 0.125 | 0.5 |
| C. difficile SK & F 3065 | 0.25 | 0.25 | 0.25 | 1.0 |
| C. difficile SK & F 3092 | 0.25 | 0.25 | 0.5 | 0.5 |
| C. difficile SK & F 3141 | 0.5 | 0.25 | 0.5 | 1.0 |

The in vivo activity of the AAD 216 aglycone, AAD 216 pseudo-aglycone, AAD 216A pseudo-aglycone and vancomycin, measured as $ED_{50}$, was demonstrated against intraperitoneal infections with 46.8 $LD_{50}$'s of Staph. aureus HH 127 in mice by treatments with the antibiotics s.c., 1 and 5 hours post infection. The $ED_{50}$'s were as follows: AAD 216 aglycone, 7.6 mg/kg; AAD 216 pseudo-aglycone, 7.6 mg/kg; AAD 216A pseudo-aglycone, 5.0 mg./kg; vancomycin, 1.56 mg/kg. Similarly, the $ED_{50}$'s of AAD 216A pseudo-aglycone, AAD 216B pseudo-aglycone, AAD 216C pseudo-aglycone and vancomycin, determined by utilizing a similar protocol, were 12.5 mg/kg, 7.6 mg/kg, 10.8 mg/kg and 1.92 mg/kg, respectively.

The antibiotic compounds of the present invention including AAD 216 aglycone, AAD 216 pseudo-aglycone, and AAD 216A pseudo-aglycone, AAD 216B pseudo-aglycone, AAD 216C pseudo-aglycone and mixtures thereof, exhibit antibacterial activity. The invention includes within its scope pharmaceutical compositions containing at least one of the above-mentioned antibiotic compounds and a pharmaceutically acceptable carrier. The compositions may also contain other active antibacterial agents. The compositions may be made up in any pharmaceutical form appropriate for the route of administration in question. Such compositions are exemplified by solid compositions for oral administration, such as tablets, capsules, pills, powders and granules; liquid compositions for oral administration such as solutions, suspensions, syrups and elixers; and preparations for parenteral administration such as sterile solutions, suspensions or emulsions.

For use as an antibacterial agent, the compositions are administered so that the concentration of the active ingredient is greater than the minimum inhibitory concentration for the particular organism treated.

The activity of the AAD 216 aglycone, AAD 216 pseudo-aglycone and AAD 216A pseudo-aglycone was demonstrated in vitro against a total of 58 bovine mastitis isolates using the conventional agar dilution method to determine minimum inhibitory concentrations (MICs). The MICs for AAD 216 aglycone, AAD 216 pseudo-aglycone and AAD 216A pseudo-aglycone ranged from 0.5 to >128 μg/ml, 0.25 to >128 μg/ml and 0.03 to >128 μg/ml, respectively. In comparison, vancomycin has MICs for the same microorganisms ranging from 0.25 to >128 μg/ml.

GROWTH PROMOTANT ACTIVITY

The growth promotant activities of the AAD 216 aglycone, AAD 216 pseudo-aglycone, and AAD 216A pseudo-aglycone were determined in a swine in vitro model to predict utility in monogastric animals, such as swine and poultry; and a rumen in vitro model to predict utility in beef, diary and sheep production.

SWINE IN VITRO MODEL

A Yorksire barrow is surgically prepared either with an ileal cannula, which is placed 15 cm. from the ileocecocolic junction, or a cecal cannula, which placed midway between the apex and origin of the cecum. The animal is fed 4 times daily restrict intake to 4.5% of body weight in a 30 kg animal or 2.5% of body weight in a 100 kg animal. The swine grower ration is:

| | (% w/w) | (lbs/ton) |
|---|---|---|
| Medium ground shelled corn | 70.60 | 1412 |
| Soybean meal, 44% | 22.00 | 440 |
| Dehydrated alfalfa meal, 17% | 4.50 | 90 |
| Calcium propionate | 0.15 | 3 |
| Vitamin/mineral premix | 2.75 | 55 |

Sampling of the material, via the cannula, begins 150–180 minutes following the first morning feeding and continues any time from 30–120 minutes thereafter, depending on the quantity of material needed. The sample is maintained in crushed ice, no cooler than 5° C., and is gassed continuously with carbon dioxide. The collected material is filtered. The filtrate is the inoculum used for incubations of the test and control samples. The gassed inoculum, 2.25 ml, is placed in each of 10 gassed test tubes, each containing 0.75 ml of a nutrient solution and 0.5 mg of each test compound. Four blank control tubes, along with the test compound tubes, are incubated 5 hours at 37° C. with agitation. Four more killed tubes are included which are not incubated.

The tubes are each treated with 0.60 ml of a 25% solution of metaphosphoric acid, then, stored at −4° C. until analysis. Samples are thawed and centrifuged for 25 minutes at 20,000 r.p.m. The supernatent liquid is decanted, sampled for gas chromatography and automatic analysis. The results are fed into a computer for finishing to give figures in which the blank control value is 100%; see the following tables. Virginiamycin and vancomycin or avoparcin are used as positive controls.

| Compound (ppm) | VFA* (% Control) | LYS* (% Control) | GLU* (% Control) | LAC* (% Control) |
|---|---|---|---|---|
| I. | | | | |
| Virginiamycin | | | | |
| (166.67) | 93 | 163 | 197 | 81 |
| (16.67) | 130 | 127 | 191 | 76 |
| (1.67) | 248 | 82 | 182 | 70 |
| Vancomycin | | | | |
| (166.67) | 250 | 48 | 190 | 64 |
| (16.67) | 280 | 42 | 189 | 59 |
| (1.67) | 92 | 83 | 100 | 99 |
| AAD 216 Aglycone | | | | |
| (166.67) | 255 | 65 | 180 | 62 |
| (16.67) | 307 | 39 | 182 | 58 |
| (1.67) | 86 | 91 | 94 | 101 |
| AAD 216 Pseudo-aglycone | | | | |
| (166.67) | 266 | 64 | 183 | 62 |
| (16.67) | 238 | 76 | 171 | 69 |
| (1.67) | 96 | 110 | 94 | 101 |
| AAD 216A Pseudo-aglycone | | | | |
| (166.67) | 302 | 52 | 187 | 58 |
| (16.67) | 361 | 59 | 184 | 50 |
| (1.67) | 106 | 106 | 101 | 98 |
| II. | | | | |
| Virginiamycin | | | | |
| (1.67) | 240 | 96 | 837 | 21 |
| Avoparcin | | | | |
| (1.67) | 85 | 101 | 115 | 102 |
| AAD 216B Pseudo-aglycone | | | | |
| (16.67) | 313 | 96 | 894 | 16 |
| (1.67) | 118 | 102 | 169 | 95 |
| AAD 216C Pseudo-aglycone | | | | |
| (16.67) | 252 | 91 | 895 | 16 |
| (1.67) | 131 | 94 | 225 | 85 |

*VFA refers to the total of volatile fatty acids, namely acetate, propionate, isobutyrate, butyrate, isovalerate and valerate.
LYS is lysine, GlU is glucose and LAC is L-lactic acid.

RUMEN IN VITRO MODEL

The protocol for the rumen in vitro model is analogous to the protocol for the swing in vitro model with the following modifications:

(1) A 400 kg steer is surgically prepared with a rumen cannula.

(2) The animal is fed one time a day with the following ration:

| | % w/w |
|---|---|
| Finished Feed | |
| Cottonseed hulls | 44.0 |
| Cracked corn | 22.0 |
| Alfalfa Hay 1" | 20.0 |
| Pellet Supplement* | 10.0 |
| Liquid Molasses | 4.0 |
| | 100.0 |
| *Pellet Supplement | |
| Soybean Oil Meal (50% protein) | 50.0 |
| Medium Ground Corn | 32.5 |
| D/Calcium Phosphate | 6.50 |
| Plain salt | 2.50 |
| Ground limestone (Thomasville) | 3.50 |
| Urea | 2.50 |
| Vitamin A & $D_2$ Premix** | 2.50 |
| | 100.00 |
| **Vitamin A & $D_2$ Premix | |
| Vitamin A (30,000 IU/gm) | 5.87 |
| Vitamin $D_2$ (16,000,000 IU/lb) | 0.50 |
| Fine ground corn | 93.63 |
| | 100.00 |

(3) Manipulation of VFA production is described as the production ratio of propionate as a percentage of total VFA produced.

(4) Sampling of the material, via the cannula, is at 120 minutes post feeding.

| Compound (ppm) | VFA* (% Control) | LYS* (% Control) | GLU* (% Control) | Propionate % (% Control) |
|---|---|---|---|---|
| III. | | | | |
| Vancomycin | | | | |
| (50.0) | 107 | 97 | 189 | 127 |
| (5.0) | 108 | 85 | 165 | 130 |
| (0.5) | 97 | 83 | 17 | 105 |
| Avoparcin | | | | |
| (50.0) | 113 | 97 | 141 | 132 |
| (5.0) | 105 | 85 | 166 | 121 |
| (0.5) | 103 | 96 | 116 | 106 |
| Monensin Sodium | | | | |
| (50.0) | 109 | 147 | 0 | 156 |
| (5.0) | 104 | 141 | 126 | 149 |
| (0.5) | 94 | 109 | 11 | 119 |
| AAD 216 Aglycone | | | | |
| (50.0) | 93 | 99 | 14 | 135 |
| (5.0) | 110 | 101 | 22 | 131 |
| (0.5) | 100 | 98 | 0 | 102 |
| AAD 216 Pseudo-aglycone | | | | |
| (50.0) | 104 | 101 | 104 | 127 |
| (5.0) | 95 | 96 | 0 | 115 |
| (0.5) | 88 | 118 | 47 | 101 |
| AAD 216A Pseudo-aglycone | | | | |
| (50.0) | 113 | 115 | 38 | 149 |
| (5.0) | 110 | 97 | 30 | 139 |
| (0.5) | 98 | 102 | 534 | 106 |
| IV. | | | | |
| Avoparcin | | | | |
| (5.0) | 109 | 157 | | 122 |
| Monensin Sodium | | | | |
| (5.0) | 106 | 595 | | 161 |
| AAD 216B Pseudo-aglycone | | | | |
| (5.0) | 114 | 163 | | 125 |
| (0.5) | 100 | 55 | | 99 |
| AAD 216C Pseudo-aglycone | | | | |

| Compound (ppm) | VFA* (% Control) | LYS* (% Control) | GLU* (% Control) | Propionate % (% Control) |
|---|---|---|---|---|
| (5.0) | 104 | 99 | 133 | |
| (0.5) | 104 | 65 | 100 | |

*VFA refers to the total of volatile fatty acids, namely acetate, propionate, isobutyrate, butyrate, isovalerate and valerate.
LYS is lysine, and GLU is glucose.

The feed compositions of this invention comprise the normal feed rations of the meat and milk producing animals supplemented by a quantity of an active ingredient selected from the group consisting of AAD 216 aglycone, AAD 216 pseudo-aglycone, AAD 216A pseudo-aglycone, AAD 216B pseudo-aglycone, AAD 216C pseudo-aglycone or a mixture thereof which is effective for improving the growth rate and feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the compound of formula I or the type of feed ration used as the basal feed.

Representative feed rations for swine and poultry are as follows:

A swine ration for growing hogs of 40-100 pounds body weight is prepared using the following formula:
Corn, ground: 78.15%
Soybean oil meal, 44%: 17.0%
Meat scraps, 50%: 3.0%
Oyster shell flavor: 0.4%
Bone meal: 0.5%
Zinc oxide: 0.01%
Vitamin A, B, $B_{12}$ & D: optional supplement A chicken ration for broilers is prepared using the following formula:
Yellow corn meal: 67.35%
Soybean oil meal: 24.00%
Menhaden fish meal: 6.00%
Steamed bone meal: 1.00%
Ground limestone: 1.00%
Iodized salt: 0.34%
25% choline chloride: 0.13%
Vitamin $B_{12}$: 0.10%
Manganese sulfate: 0.02%
Vitamin mix: 0.06%

Swine feed from weanling to fattening or finishing rations may be supplemented. Swine eat from about 2 lb. of ration per day (for a 25 lb. pig) to 9 lb. per day (for a 150 lb. pig). Most rations are comprised of a corn base supplemented with legume silage, wheat bran, oats barley, molasses or a protein supplement.

Poultry feeds comprise starter rations, broiler rations and laying rations. The rations are usually based on ground corn, corn meal or soybean meal. The broiler rations, often, contain high energy supplements such as added fats, proteins and vitamins. Turkey rations are similar, but comprise only a starting ration and a growing ration. Chickens or pheasants eat from 0.03-0.3 lbs. of feed per day, turkeys twice that much. Estimated intake of feed is dependent on the weight and age of the meat producing animal.

The active ingredients selected from the group consisting of AAD 216 aglycone. AAD 216 pseudo-aglycone, AAD 216A pseudo-aglycone, AAD 216B pseudo-aglycone, AAD 216C pseudo-aglycone or a mixture thereof are mixed uniformly with such feed rations to give supplemented rations which are, then fed as to custom, which is, most often, ad libitum. Conveniently, to do this, a premix of the supplemental growth promotant of this invention, optionally combined with or without other supplements known to this art such as an anthelmintic, a nitrogen source or an antibiotic, for example, virginiamycin or oxytetracycline is prepared by the manufacturer for sale to the formulators or feed lot operators. The concentration of the active ingredients selected from the group consisting of AAD 216 aglycone, AAD 216 pseudo-aglycone, AAD 216A pseudo-aglycone, AAD 216B pseudo-aglycone, AAD 216C pseudo-aglycone or a mixture thereof in the premix is usually from 5-75% by weight or a concentration 100-2000 times greater than that in the complete feed ration. The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ration which is fed to the target animal. Such premix compositions are included in the term "feed compositions" as used herein.

The concentration of the active ingredients selected from the group consisting of AAD 216 aglycone, AAD 216 pseudo-aglycone, AAD 216A pseudo-aglycone, AAD 216B pseudo-aglycone, AAD 216C pseudo-aglycone or a mixture thereof in the complete ration is a nontoxic but active quantity chosen, for example, from a range of about 1-1000 parts of active ingredient by weight per million parts of whole feed (ppm) or about 2-115 grams per ton. Advantageously, a nontoxic quantity of active ingredient is chosen from the range of 10-50 ppm.

The method of this invention comprises feeding to monogastric or ruminant, meat or milk producing animals, especially beef and dairy cattle, sheep, swine and poultry, an effective growth promoting but nontoxic quantity of an active ingredient selected from the group consisting of AAD 216 aglycone, AAD 216 pseudo-aglycone, AAD 216A pseudo-aglycone, AAD 216B pseudo-aglycone, AAD 216C pseudo-aglycone or a mixture thereof. Other monogastric animals whose digestive tract also features fermentation in a cecum or cecum-like chamber are rabbits and horses.

The supplemented feed rations, described above, are presented to the animal by methods known to the art. Ad libitum feeding in the pasture, pen or growing shed is most convenient to increase the growth and milking rate of the animal and to increase the feed efficiency of the operation.

The following examples are illustrative of the production, isolation and purification of the antibiotics of the present invention and are not therefore to be considered in limiting the present invention as described in the claims appended hereto.

EXAMPLE 1

Preparation of AAD 216 pseudo-aglycone

AAD 216A (1.2 g) was partially dissolved in 10 percent aqueous acetonitrile and 0.001N hydrochloric acid (total volume 1500 ml) and heated to reflux for 48 hours. The reaction mixture was lyophilized and then chromatographed on reverse phase HPLC with a column of Whatman Partisil 40 ® (ODS-3) (25×500 mm)

at a flow rate of 15 ml/minute. The column was eluted with 15 percent acetonitrile—0.1M pH 3.2 phosphate buffer (2000 ml) and 18 percent acetonitrile-buffer solution (1000 ml). The appropriate fractions were combined, lyophilized and desalted as described below to yield the desired AAD 216 pseudo-aglycone.

The desalting procedure involved a pooling of the appropriate fractions from the HPLC and removal of the acetonitrile at reduced pressure. The resulting aqueous samples were loaded onto an XAD-7 resin column and eluted with deionized water until the conductivity of the outflow was less than 1.5 μMHO. The column was then eluted with aqueous acetonitrile (50%) and the eluant lyophilized to afford the desired products.

EXAMPLE 2

Preparation of AAD 216 aglycone and AAD 216A pseudo-aglycone

AAD 216A (0.75 g.) was dissolved in 5 percent concentrated hydrochloric acid and dimethylsulfoxide (40 ml) and heated for 15 minutes at 100° C. The reaction mixture was diluted with 14 percent acetonitrile 0.1M pH 3.2 phosphate buffer and chromatographed with the equipment described in Example 1. The column was eluted with 14 percent acetonitrile-buffer solution (1000 ml) followed by 18 percent (500 ml), 22 percent (500 ml), 26 percent (500 ml) and 30 percent (1000 ml) acetonitrile-buffer solution. The appropriate fractions containing AAD 216A pseudo-aglycone were combined and the appropriate fractions containing AAD 216 aglycone were combined. Both of the combined fractions were separately lyophilized and desalted using the procedure in Example 1 to afford the desired products.

EXAMPLE 3

Preparation of AAD 216B Pseudo-Aglycone

AAD 216B (1.64 g) was dissolved in dimethylsulfoxide (40 ml) and concentrated hydrochloric acid (2 ml) was added. The reaction mixture was heated at 100° C. for 15 minutes and then diluted with 31 percent acetonitrile 0.1M pH 6.0 phosphate buffer (450 ml) which was loaded onto an affinity chromatography column (700 ml-Affigel 10 D-ala-D-ala). The column was washed with 0.1M pH 6.0 phosphate buffer (1000 ml), water (2000 ml) and 1 percent aqueous acetonitrile (1000 ml). The reaction products were eluted off the affinity chromatography column with 50 percent acetonitrile in 0.15N ammonia (2000 ml). The eluant was lyophilized, dissolved in 10 percent acetonitrile in 0.1M pH 6.0 phosphate buffer and chromatographed on the equipment described in Example 1. The column was eluted with 10 percent acetonitrile in 0.1M pH 6.0 phosphate buffer (500 ml), followed by 15 percent (750 ml), 18 percent (750 ml), 22 percent (500 ml), 26 percent (50 ml), 30 percent (500 ml) and 35 percent (1000 ml) acetonitrile buffer solution. The appropriate factions containing AAD 216B pseudo-aglycone were combined and the fractions containing AAD 216 aglycone were combined. Both combined fractions were separately lyophilized and desalted using the procedure in Example 1 to afford the desired products.

Utilizing the procedure of Example 3, AAD 216C (2.0 g) was hydrolyzed to yield AAD 216C pseudo-aglycone and AAD 216 aglycone. AAD 216A pseudo-aglycone was also prepared via the procedure of Example 3.

What is claimed is:

1. An antibiotic compound represented by the structural formula (I)

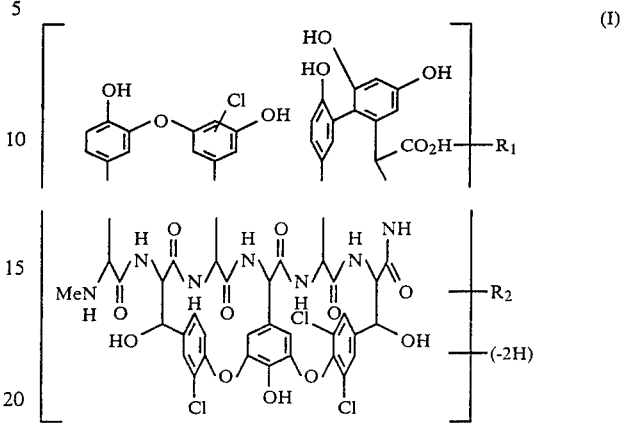

wherein $R_1$ is hydrogen or mannosyl and $R_2$ is hydrogen or a glycolipid radical of unknown structure with the proviso that at least one of $R_1$ and $R_2$ is hydrogen, prepared by the partial acidic hydrolysis of an antibiotic selected from the group consisting of AAD 216 complex, AAD 216A, AAD 216B and AAD 216C.

2. An antibiotic compound represented by the structural formula (I)

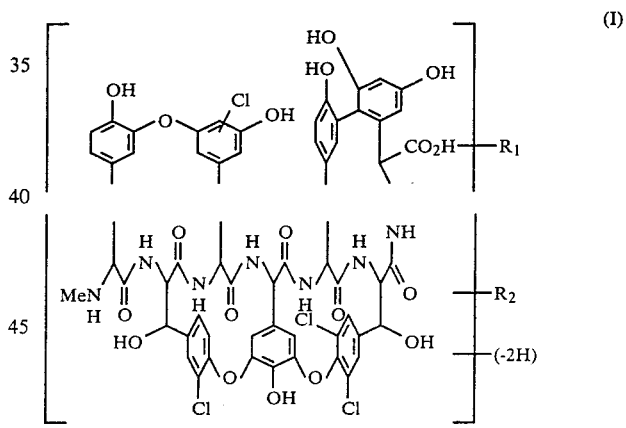

wherein $R_1$ is mannosyl and $R_2$ is hydrogen having the following characteristics:
  (a) pale white-yellow solid which decomposes at 300°–350° C.;
  (b) an empirical formula $C_{65}H_{55}N_7O_{24}Cl_4$;
  (c) an approximate elemental composition of 47.54 percent carbon, 4.00 percent hydrogen, 5.89 percent nitrogen and 8.63 percent chlorine when the water content was 12 percent;
  (d) an infrared absorption spectrum in potassium bromide which exhibits peaks at the following wave numbers in cm$^{-1}$: 3400, 1660, 1610, 1590, 1510, 1460, 1430, 1390, 1300, 1230, 1180, 1150, 1120, 1060, 1010, 970 and 810;
  (e) a fast atom bombardment (FAB) mass spectrum with M+H at 1458 (major cluster);
  (f) an ultraviolet spectrum in acetonitrile:water (1:1) which exhibits an absorption maximum at 281 nm 4,521,335 under acid conditions with an $E_{1\%}=79.7$ and at 300 nm under basic conditions with an $E_{1\%}=136$;

(g) a carbon magnetic resonance spectrum at 90.56 MHz in $CD_3OD:D_2O$ (1:9) at a pH of 8.7 which exhibits the following chemical shifts in parts per million (ppm) relative to TMS as standard: 177.9, 174.6, 171.7, 170.9, 170.0, 169.2, 162.3, 158.8, 157.9, 155.2, 155.1, 153.9, 151.9, 149.7, 147.6, 147.2, 144.4, 141.0, 139.0, 138.8, 137.5, 136.1, 134.6, 130.7, 130.0, 129.8, 129.2, 128.9, 128.7, 127.5, 127.3, 126.9, 126.4, 126.0, 125.2, 122.7, 122.2, 121.1, 119.9, 119.7, 118.4, 116.6, 110.7, 110.4, 108.5, 104.4, 103.3, 100.5, 98.1, 74.0, 72.1, 71.6, 71.4, 70.8, 67.4, 65.8, 63.7, 62.2, 61.6, 60.2, 56.0, 55.9, 55.0 and 32.9 and (h) $pK_a$ values in acetonitrile:water (3:7) as follows: 3.3, 7.1, 8.3, 9.1, 10.0 and 11.2 $pK_a$ values above 11.2 not determined.

3. An antibiotic compound represented by the structural formula (I)

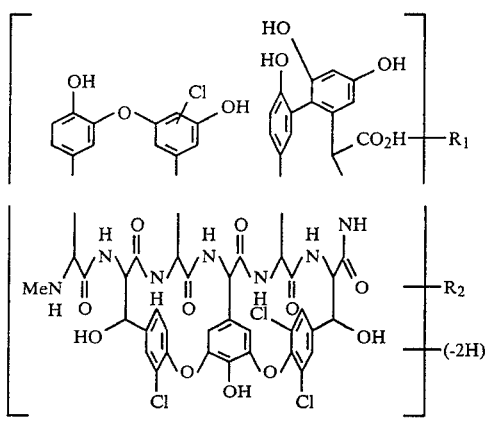

wherein $R_1$ is hydrogen and $R_2$ is a glycolipid of unknown structure having an empirical formula $C_{16}H_{28}NO_6$ and having the following characteristics:

(a) pale white-yellow solid which decomposes at 300°-350° C.;
(b) an empirical formula $C_{75}H_{72}N_8O_{25}Cl_4$;
(c) an approximate elemental composition of 49.76 percent carbon, 4.51 percent hydrogen, 5.99 percent nitrogen and 8.19 percent chlorine when the water content was 9.4 percent;
(d) an infrared absorption spectrum in potassium bromide which exhibits peaks at the following wave numbers in $cm^{-1}$: 3400, 2920, 1660, 1590, 1500, 1460, 1430, 1300, 1240, 1140, 1080, 1060 and 1010;
(e) a fast atom bombardment (FAB) mass spectrum with M+H at 1625 (major cluster);
(f) an ultraviolet spectrum in acetonitile:water (1:1) which exhibits an absorption maximum at 281 nm under acidic conditions with an $E_{1\%}=63.2$ and at 302 nm under basic conditions with an $E_{1\%}=94$;
(g) a carbon magnetic resonance spectrum at 90.56 MHz in $CD_3OD:D_2O$ (1:9) at a pH of 9.4 which exhibits the following chemical shifts in parts per million (ppm) relative to TMS as standard: 178.2, 178.0, 176.0, 175.6, 171.6, 170.9, 170.6, 170.5, 169.3, 164.6, 161.4, 159.3, 157.1, 156.5, 153.5, 152.5, 151.8, 151.1, 146.4, 144.9, 141.7, 138.6, 138.4, 136.9, 134.5, 134.4, 133.9, 130.8, 129.8, 129.7, 129.4, 128.6, 128.5, 128.3, 127.7, 127.3, 125.9, 125.7, 125.5, 122.5, 122.1, 120.1, 119.4, 118.0, 116.9, 109.6, 109.0, 108.7, 104.5, 104.4, 103.2, 98.9, 78.4, 74.3, 73.3, 72.1, 71.5, 66.2, 63.7, 61.9, 60.6, 56.9, 56.1, 55.8, 55.4, 37.2, 33.3, 32.0, 29.6, 29.4, 26.1, 22.9 and 14.4; and (h) $pK_a$ values in acetonitrile:water (3:7) as follows: 3.0, 4.3, 7.4, 8.5, 9.9 and 10.9 $pK_a$ values above 10.9 not determined.

4. An antibiotic compound represented by the structural formula (I)

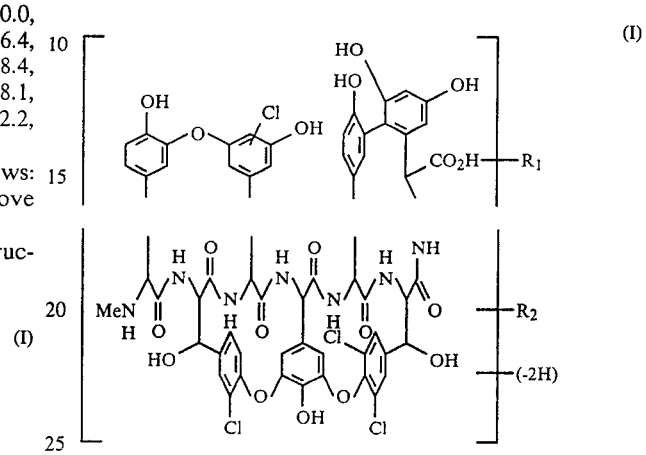

wherein $R_1$ is hydrogen and $R_2$ is a glycolipid radical of unknown structure having an empirical formula $C_{17}H_{30}NO_6$ has the following characteristics:

(a) white solid which decomposes at 250°-300° C.;
(b) an empirical formula $C_{76}H_{74}N_8O_{25}Cl_4$;
(c) an approximate elemental composition of 48.98 percent carbon, 4.56 percent hydrogen, 5.64 percent nitrogen and 8.29 percent chlorine when the water content was 6.9 percent;
(d) an infrared absorption spectrum in potassium bromide which exhibits peaks at the following wave numbers in $cm^{-1}$: 3400, 2920, 1660, 1590, 1500, 1480, 1430, 1300, 1240, 1150, 1080, 1060 and 1010;
(e) a fast atom bombardment (FAB) mass spectrum with M+H at 1639 (major cluster);
(f) an ultraviolet spectrum in acetonitrile:water (1:1) which exhibits an absorption maximum at 281 nm under acidic conditions with an $E_{1\%}=61.8$ and at 303 nm under basic conditions with an $E_{1\%}=88$;
(g) a carbon magnetic resonance spectrum at 90.56 MHz in $CD_3OD:D_2O$ (1.9) at a pH of 9.4 which exhibits the following chemical shifts in parts per million (ppm) relative to TMS as standard: 178.3, 177.6, 175.9, 175.6, 171.5, 171.0, 170.7, 170.3, 169.4, 164.0, 159.3, 158.9, 156.4, 152.5, 151.7, 151.1, 146.2, 144.7, 141.8, 138.7, 138.6, 136,8, 134.4, 133.8, 130.9, 129.8, 129.5, 128.6, 128.4, 127.9, 127.3, 126.0, 125.8, 122.5, 119.9, 119.3, 118.2, 116.9, 109.3, 108.8, 104.3, 104.2, 103.0, 99.4, 78.7, 74.4, 73.5, 72.1, 71.6, 65.8, 63.8, 62.5, 60.6, 57.1, 56.1, 55.9, 55.4, 39.7, 37.3, 33.1, 30.3, 29.9, 29.7, 28.5, 28.0 26.3 and 23.4.

5. An antibiotic compound represented by the structural formula (I)

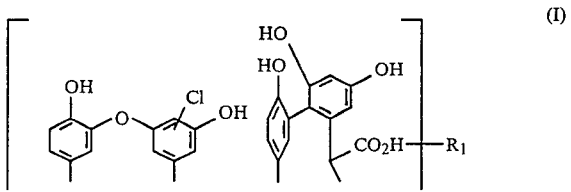

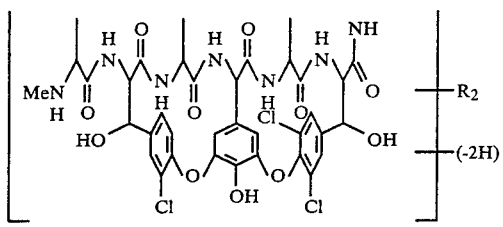

wherein $R_1$ is hydrogen and $R_2$ is a glycolipid radical of unknown structure having an empirical formula $C_{18}H_{32}NO_6$ has the following characteristics:

(a) white solid which decomposes at 250°–300° C.;
(b) an empirical formula $C_{77}H_{76}N_8O_{25}Cl_4$;
(c) an approximate elemental composition of 47.58 percent carbon, 4.51 percent hydrogen, 5.33 percent nitrogen and 8.08 percent chlorine when the water content was 7.8 percent;
(d) an infrared absorption spectrum in potassium bromide which exhibits peaks at the following wave numbers in $cm^{-1}$: 3400, 2920, 1660, 1590, 1500, 1430, 1300, 1240, 1140, 1080, 1060 and 1010;
(e) a fast atom bombardment (FAB) mass spectrum with M+H at 1653 (major cluster);
(f) an ultraviolet spectrum in acetonitrile:water (1:1) which exhibits an absorption maximum at 281 nm under acidic conditions with an $E_{1\%}=60.0$ and at 303 nm under basic conditions with an $E_{1\%}=83$;
(g) a carbon magnetic resonance spectrum at 90.56 MHz in $CD_3OD:D_2O$ (1:9) at a pH of 9.4 which exhibits the following chemical shifts in parts per million (ppm) relative to TMS as standard: 178.1, 177.4, 175.5, 175.4, 171.4, 171.0, 170.7, 170.3, 169.3, 163.6, 159.1, 158.6, 156.5, 156.2, 152.7, 151.9, 151.8, 151.0, 146.2, 144.6, 142.0, 138.8, 138.6, 136.9, 134.8, 134.7, 134.0, 130.6, 129.9, 129.8, 129.4, 128.8, 128.3, 127.8, 127.5, 127.2, 126.4, 126.2, 125.8, 122.5, 122.0, 119.6, 119.1, 118.4, 116.9, 109.5, 109.2, 108.7, 104.2, 103.6, 98.8, 78.6, 74.6, 73.5, 72.1, 71.7, 66.0, 63.7, 62.1, 60.6, 56.9, 56.1, 55.9, 55.4, 39.6, 37.3, 33.2, 30.4, 30.0, 29.8, 28.5, 27.9, 26.3 and 23.1.

6. An antibiotic compound represented by the structural formula (II)

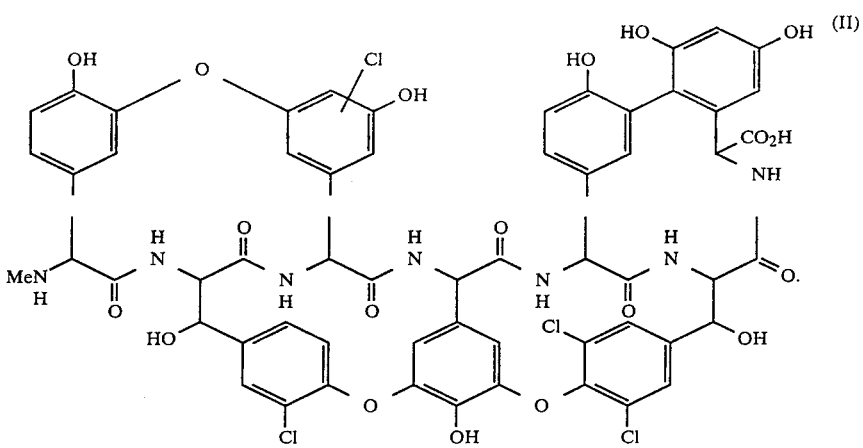

UNITED STATES PATENT AND TRADEMARK OFFICE
CERTIFICATE OF CORRECTION

PATENT NO. : 4,521,335
DATED : June 4, 1985
INVENTOR(S) : George W. Chan and Robert D. Sitrin It is certified that error appears in the above-identified patent and that said Letters Patent are hereby corrected as shown below:

At column 1, lines 46-63; at column 16, lines 5-20; at column 16, lines 34-49; at column 17, lines 20-36; and at column 18, lines 10-25, correct the structural formula to appear as follows:

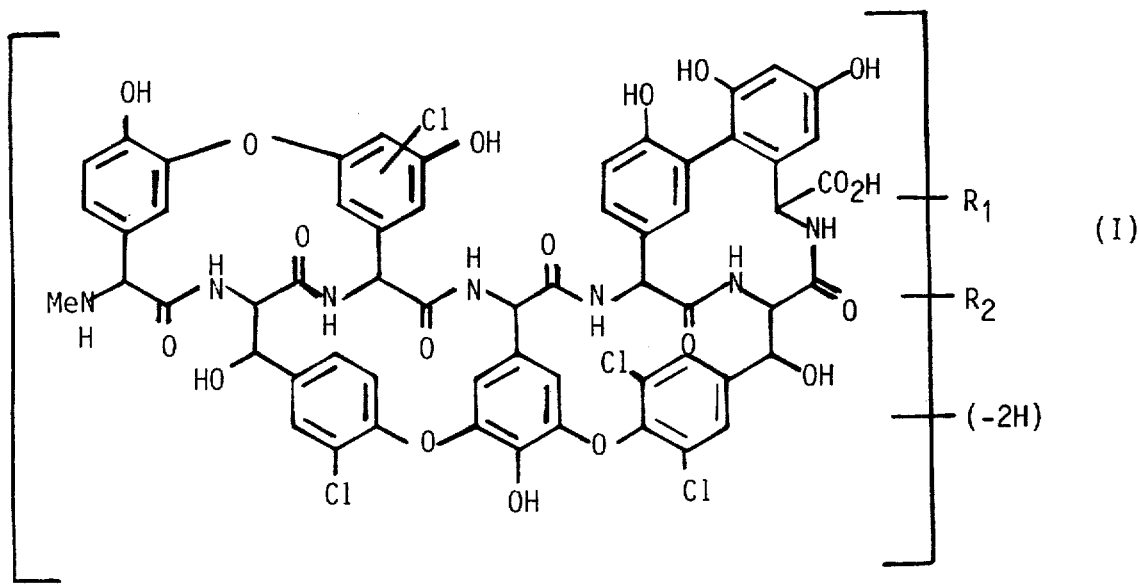

UNITED STATES PATENT AND TRADEMARK OFFICE
CERTIFICATE OF CORRECTION

PATENT NO.    : 4,521,335                       Page 2 of 2
DATED         : June 4, 1985
INVENTOR(S)   : George W. Chan and Robert D. Sitrin It is certified that error appears in the above-identified patent and that said Letters Patent is hereby corrected as shown below:

At columns 5 and 6, lines 34-52 and at columns 19 and 20, lines 25-45, correct the structural formula to appear as follows:

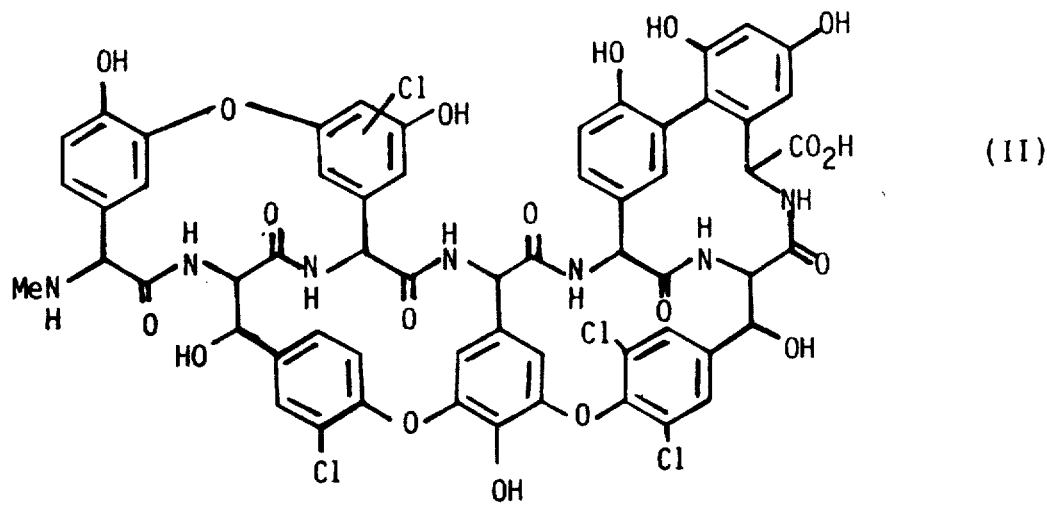

(II)

Signed and Sealed this

Eleventh Day of March 1986

[SEAL]

Attest:

DONALD J. QUIGG

Attesting Officer     Commissioner of Patents and Trademarks